United States Patent
Nedblake et al.

(10) Patent No.: US 8,498,880 B2
(45) Date of Patent: Jul. 30, 2013

(54) SHARED PROTOCOL STATEMENTS

(75) Inventors: Ginger H. Nedblake, Liberty, MO (US); Mark A. Hoffman, Lee's Summit, MO (US); Kevin M. Power, Kansas City, MO (US)

(73) Assignee: Cerner Innovation, Inc., Lenexa, KS (US)

( * ) Notice: Subject to any disclaimer, the term of this patent is extended or adjusted under 35 U.S.C. 154(b) by 0 days.

(21) Appl. No.: 12/496,906

(22) Filed: Jul. 2, 2009

(65) Prior Publication Data

US 2010/0004946 A1    Jan. 7, 2010

Related U.S. Application Data

(63) Continuation of application No. 11/967,893, filed on Dec. 31, 2007, now Pat. No. 8,224,671.

(60) Provisional application No. 60/882,787, filed on Dec. 29, 2006.

(51) Int. Cl.
*G06Q 50/00*    (2012.01)

(52) U.S. Cl.
USPC .................................. 705/2; 705/3; 705/7.11

(58) Field of Classification Search
USPC ....................................... 705/2, 3, 7.11–7.42
See application file for complete search history.

(56) References Cited

U.S. PATENT DOCUMENTS

| | | | |
|---|---|---|---|
| 4,315,309 A | 2/1982 | Coli | |
| 5,845,255 A | 12/1998 | Mayaud | |
| 6,018,713 A * | 1/2000 | Coli et al. | 705/2 |
| 6,556,951 B1 * | 4/2003 | Deleo et al. | 702/183 |
| 6,607,911 B2 * | 8/2003 | Gordon et al. | 435/320.1 |
| 6,818,762 B2 * | 11/2004 | Rundell et al. | 536/23.1 |
| 7,050,933 B2 * | 5/2006 | Parvin et al. | 702/179 |
| 7,356,482 B2 * | 4/2008 | Frankland et al. | 705/7.12 |
| 7,398,171 B2 * | 7/2008 | Woo et al. | 702/82 |
| 7,756,727 B1 | 7/2010 | Greenspan et al. | |
| 2003/0036925 A1 | 2/2003 | Miller | |
| 2004/0014097 A1 | 1/2004 | McGlennen | |
| 2004/0044560 A1 | 3/2004 | Giglio et al. | |
| 2004/0053333 A1 * | 3/2004 | Hitt et al. | 435/7.1 |
| 2004/0078220 A1 | 4/2004 | Jackson | |
| 2005/0209888 A1 | 9/2005 | Oowaki | |
| 2006/0293919 A1 | 12/2006 | Morlet | |
| 2007/0083384 A1 | 4/2007 | Geslak et al. | |
| 2007/0124278 A1 * | 5/2007 | Lewis et al. | 707/2 |

(Continued)

OTHER PUBLICATIONS

NPL—Office action dated Oct. 29, 2009 from U.S. Appl. No. 11/967,893.

(Continued)

*Primary Examiner* — David Rines

(74) *Attorney, Agent, or Firm* — Shook, Hardy & Bacon L.L.P.

(57) ABSTRACT

Computerized methods and systems for creating and documenting protocol orders in a molecular diagnostic laboratory environment are provided. Utilizing the methods and systems described herein, protocol statements may require values to be entered in association therewith prior to permitting access to subsequent protocol orders. Accordingly, more accurate test runs and, consequently, more accurate test results, may be achieved. Additionally, as values associated with protocol statements are electronically captured, in accordance with embodiments hereof, such values may be searched to evaluate trends or identify protocol orders and/or results that may be affected by a later discovered error or the like.

8 Claims, 15 Drawing Sheets

U.S. PATENT DOCUMENTS

| | | |
|---|---|---|
| 2009/0106333 A1 | 4/2009 | Nedblake |
| 2009/0112934 A1 | 4/2009 | Nedblake |
| 2009/0265713 A1 | 10/2009 | Nedblake |
| 2010/0094562 A1 | 4/2010 | Shohat |
| 2010/0152622 A1 | 6/2010 | Teulings |

OTHER PUBLICATIONS

Non-Final Office Action dated Apr. 3, 2009; U.S. Appl. No. 11/967,893; filed Dec. 31, 2007.
Non-Final Office Action mailed Oct. 7, 2010 re U.S. Appl. No. 12/497,030.
Final Office Action mailed Feb. 3, 2011 re U.S. Appl. No. 11/967,893.
Final Office Action mailed Jun. 23, 2010re U.S. Appl. No. 11/967,893.
Non-Final Office Action mailed Mar. 3, 2011 re U.S. Appl. No. 12/346,998.
Non-Final Office Action mailed Apr. 14, 2011 re U.S. Appl. No. 12/497,030.
Non Final Office Action mailed Jun. 22, 2011 re U.S. Appl. No. 12/346,978.
Non Final Office Action in U.S. Appl. No. 12/346,998, mailed Nov. 6, 2012, 27 pages.
Notice of Allowance mailed Nov. 23, 2012 in U.S. Appl. No. 12/497,030, 21 pages.
Final Office Action of U.S. Appl. No. 12/346,978, mailed Feb. 2, 2012, 25 pp.
Non-Final Office Action mailed Mar. 28, 2012 re U.S. Appl. No. 12/497,030, 16 pp.
Final Office Action mailed Oct. 13, 2011 re U.S. Appl. No. 12/346,998 26 pages.
Notice of Allowance, mailed Apr. 12, 2012, in U.S. Appl. No. 11/967,893, 24 pp.
Non-Final Office dated Apr. 10, 2013 re U.S. Appl. No. 12/346,978, 22 pages.

* cited by examiner

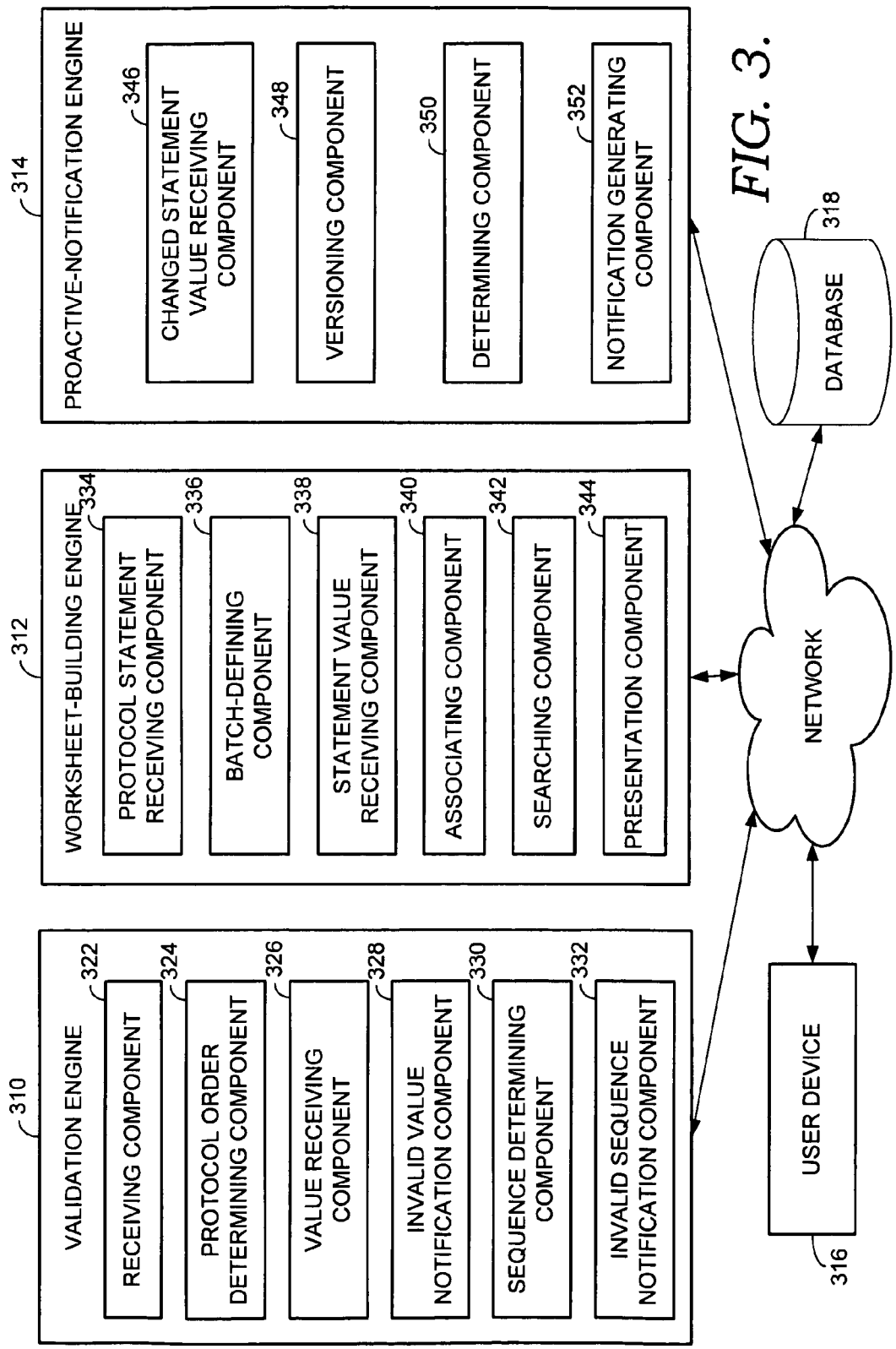

SHARED PROTOCOL STATEMENTS

CROSS-REFERENCE TO RELATED APPLICATIONS

This application is a continuation of U.S. application Ser. No. 11/967,893 filed Dec. 31, 2007, which application claims the benefit of U.S. Provisional Patent Application No. 60/882,787, filed Dec. 29, 2006, entitled "Documentation of Protocol Orders", and which applications are hereby incorporated by reference in their entirety.

STATEMENT REGARDING FEDERALLY SPONSORED RESEARCH OR DEVELOPMENT

Not Applicable.

BACKGROUND

In molecular diagnostic laboratories, there are often a number of steps that are taken between receiving a patient specimen in the laboratory and generating an ordered result from the specimen. For instance, if a clinician orders a diagnostic test to determine if a patient has a mutation in a particular gene, a specimen will be collected from the patient, e.g., from the patient's amniotic fluid, and transported to the laboratory for testing. In order for the laboratory technologist to test the specimen for a mutation in the gene of interest, a number of steps not specifically ordered by the clinician generally take place. For instance, the laboratory technologist will likely evaluate the specimen to determine if it is suitable for testing. If it is determined to be suitable, DNA will likely be isolated from the specimen. The DNA will then be evaluated by the laboratory technologist to determine if it is suitable for evaluation, e.g., utilizing the 260/280 DNA purity measure. If the DNA is determined to be suitable for evaluation, the laboratory technologist will typically use Polymerase Chain Reaction (PCR) to magnify the region of a sequence of interest (wild type or mutation). Next, the laboratory technologist will typically place the amplified PCR product on an electrophoreses gel to determine whether mutation or wild type (normal) sequence is present in one or both chromosomes. It can then be reported whether the patient has a mutation in the gene for which the clinician placed the order.

Typically, the only data elements from the above scenario that are electronically captured are the clinician's order and the result. In modern clinical settings, there is often an electronic record, e.g., an electronic medical record associated with each patient presenting at a hospital or clinic. One such electronic medical record may be generated by Cerner Millennium available from Cerner Corporation of Kansas City, Mo. When utilizing an electronic medical record, the electronically captured data elements may be stored in association with the patient's electronic medical record. Additionally, such electronically captured data elements may be stored such that they are searchable. However, those data elements which are not captured electronically, typically those data elements which are related to the workflow that takes place between the clinician placing a desired order and the results being reported, are manually entered into laboratory notebooks or the like, if the data elements are captured at all. Thus, not only are these steps not associated with the patient's medical record, they are also not searchable to identify trends, make corrections, perform audits, and the like.

BRIEF SUMMARY

Embodiments of the present invention relate to computerized methods and systems, and computer readable media having computer-executable instructions embodied thereon for performing the disclosed methods, for creating and documenting protocol orders in a molecular diagnostic laboratory environment. Utilizing the methods and systems described herein, protocol statements may require values to be entered in association therewith prior to permitting access to subsequent protocol orders. Accordingly, more accurate test runs and, consequently, more accurate test results, may be achieved. Additionally, as values associated with protocol statements are electronically captured, in accordance with embodiments hereof, such values may be searched to evaluate trends or identify protocol orders and/or results that may be affected by a later discovered error or the like.

Embodiments of the present invention further provide computerized methods and systems, and computer readable media having computer-executable instructions embodied thereon for performing the disclosed methods, for associating a plurality of protocol orders or containers with one another into a batch. Embodiments further provide for sharing of values entered in association with shared protocol statements among the members of a batch. Sharing of protocol statement values saves time for the laboratory technologist as common values, e.g., lot numbers, run temperatures, and the like, need only be input one time instead of independently entered for all members of a batch.

Additional embodiments of the present invention provide computerized methods and systems, and computer readable media having computer-executable instructions embodied thereon for performing the disclosed methods, for proactively notifying a user if a changed protocol statement or protocol statement value will affect other protocol orders and/or results. Thus, if it is discovered, for instance, that an incorrect DNA purity value range had been input when a worksheet for a particular protocol order was built or an incorrect run temperature had been input as a value associated with a particular protocol statement, upon changing the protocol statement or protocol statement value, respectively, the user will be notified of all other protocol orders and/or results that also utilized the incorrect protocol order and/or protocol statement value. The user can then quickly determine what other changes may be necessary to facilitate more accurate results reporting.

This Summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein:

FIG. 3 is a block diagram of an exemplary system suitable for use in implementing embodiments of the present invention;

FIG. 5 is an illustrative screen display of an exemplary user interface for building a protocol worksheet, in accordance with an embodiment of the present invention;

FIG. 7 is an illustrative screen display of an exemplary user interface for defining a protocol batch, in accordance with an embodiment of the present invention;

FIG. 8 is an illustrative screen display of an exemplary user interface for viewing information related to members of a protocol batch, in accordance with an embodiment of the present invention.

DETAILED DESCRIPTION

Figure 1:
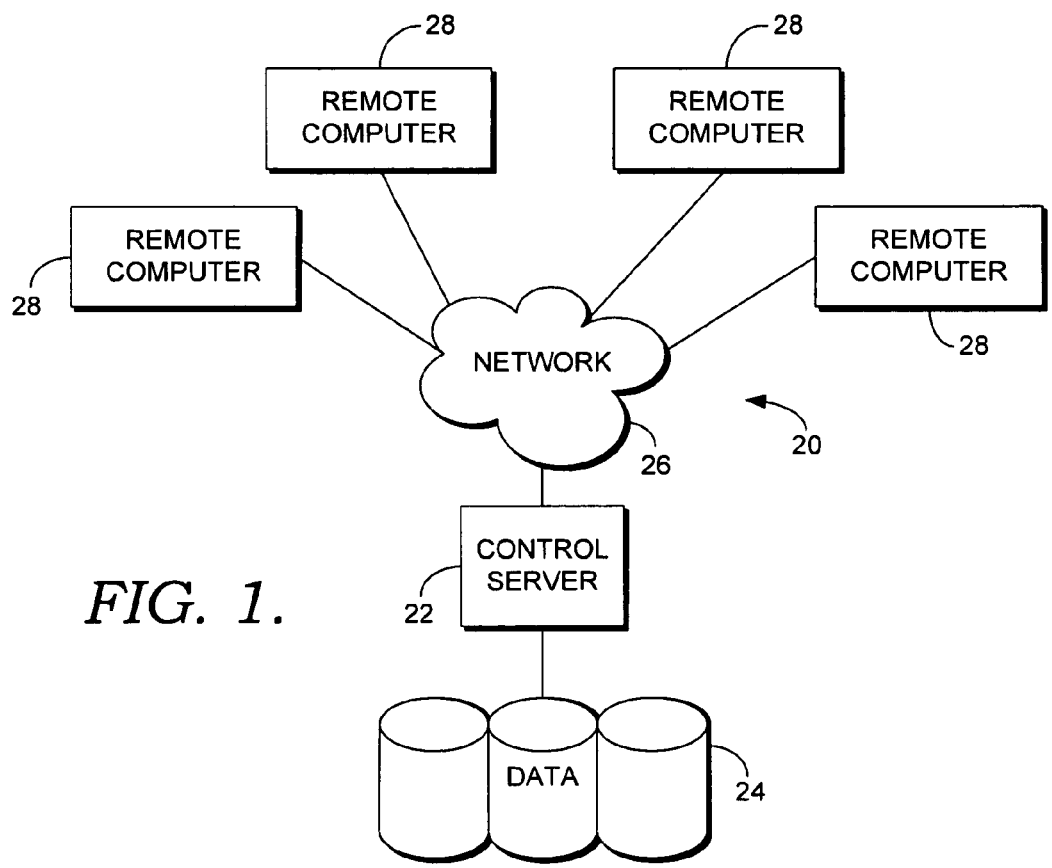
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems for creating and documenting protocol orders in a molecular diagnostic laboratory environment. Utilizing the methods and systems described herein, protocol statements may require values to be entered in association therewith prior to permitting access to subsequent protocol orders. Accordingly, more accurate test runs and, consequently, more accurate test results, may be achieved. Additionally, as values associated with protocol statements are electronically captured, in accordance with embodiments hereof, such values may be searched to evaluate trends or identify protocol orders and/or results that may be affected by a later discovered error or the like.

Embodiments of the present invention further provide computerized methods and systems for associating a plurality of protocol orders or containers with one another into a batch. Embodiments further provide for sharing of values entered in association with shared protocol statements among the members of a batch. Sharing of protocol statement values saves time for the laboratory technologist as common values, e.g., lot numbers, run temperatures, and the like, need only be input one time instead of independently entered for all members of a batch.

Additional embodiments of the present invention provide computerized methods and systems for proactively notifying a user if a changed protocol statement or protocol statement value will affect other protocol orders and/or results. Thus, if it is discovered, for instance, that an incorrect DNA purity value range had been input when a worksheet for a particular protocol order was built or an incorrect run temperature had been input as a value associated with a particular protocol statement, upon changing the protocol statement or protocol statement value, respectively, the user will be notified of other protocol orders and/or results that also utilized the incorrect protocol order and/or protocol statement value. The user can then quickly determine what other changes may be necessary to facilitate more accurate results reporting.

Having briefly described embodiments of the present invention, an exemplary operating environment suitable for use in implementing embodiments of the present invention is described below.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare-related orders, particularly, molecular diagnostic orders. As contemplated by the language above, the methods and systems of embodiments of the present invention may also be implemented on a stand-alone desktop, personal computer, or any other computing device used in a healthcare environment or any of a number of other locations.

Figure 2:
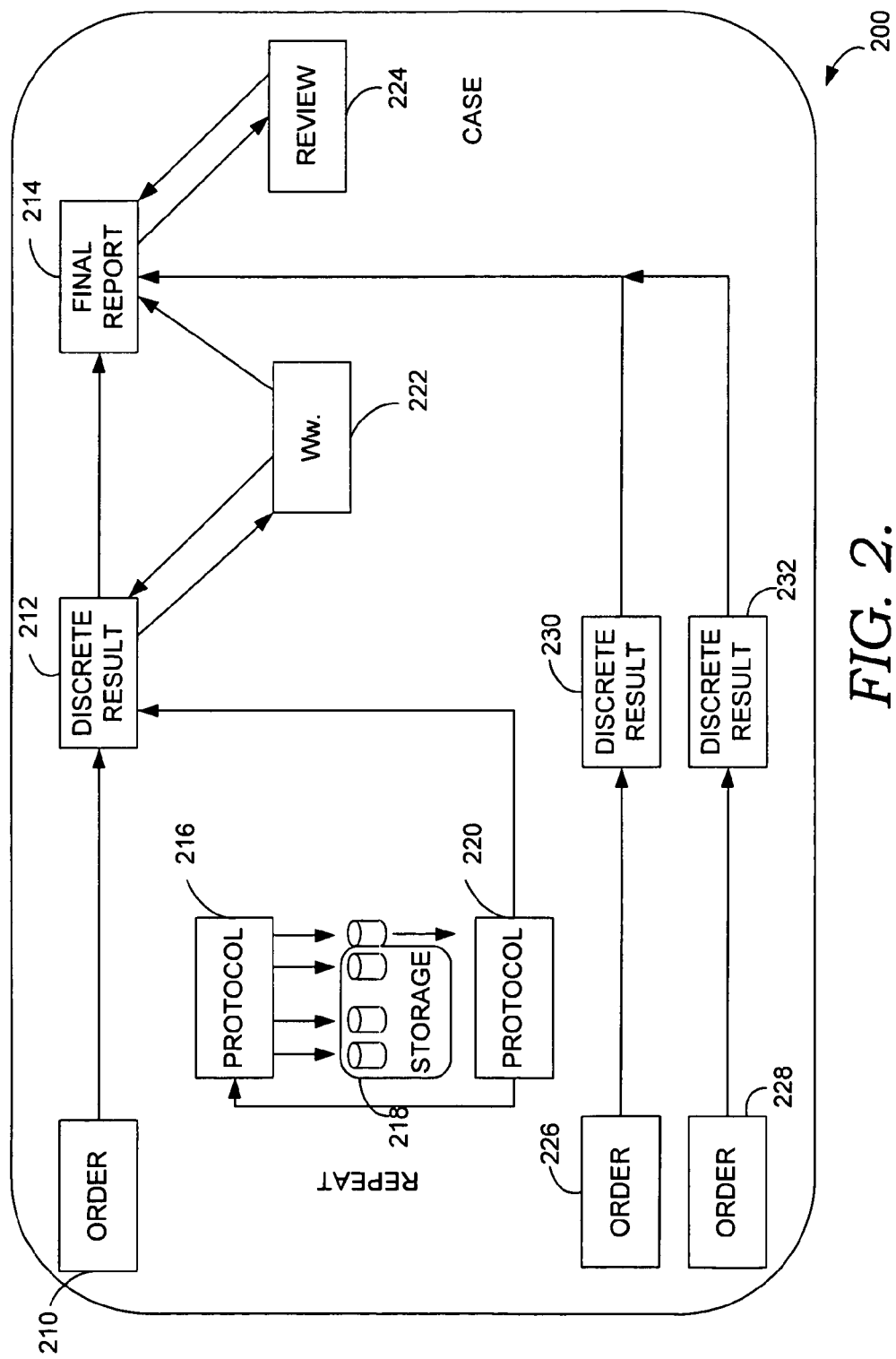
FIG. 2 is a block diagram illustrating how embodiments of the present invention alter the capture of data elements related to workflow in the diagnostic laboratory.
Figure 4A:
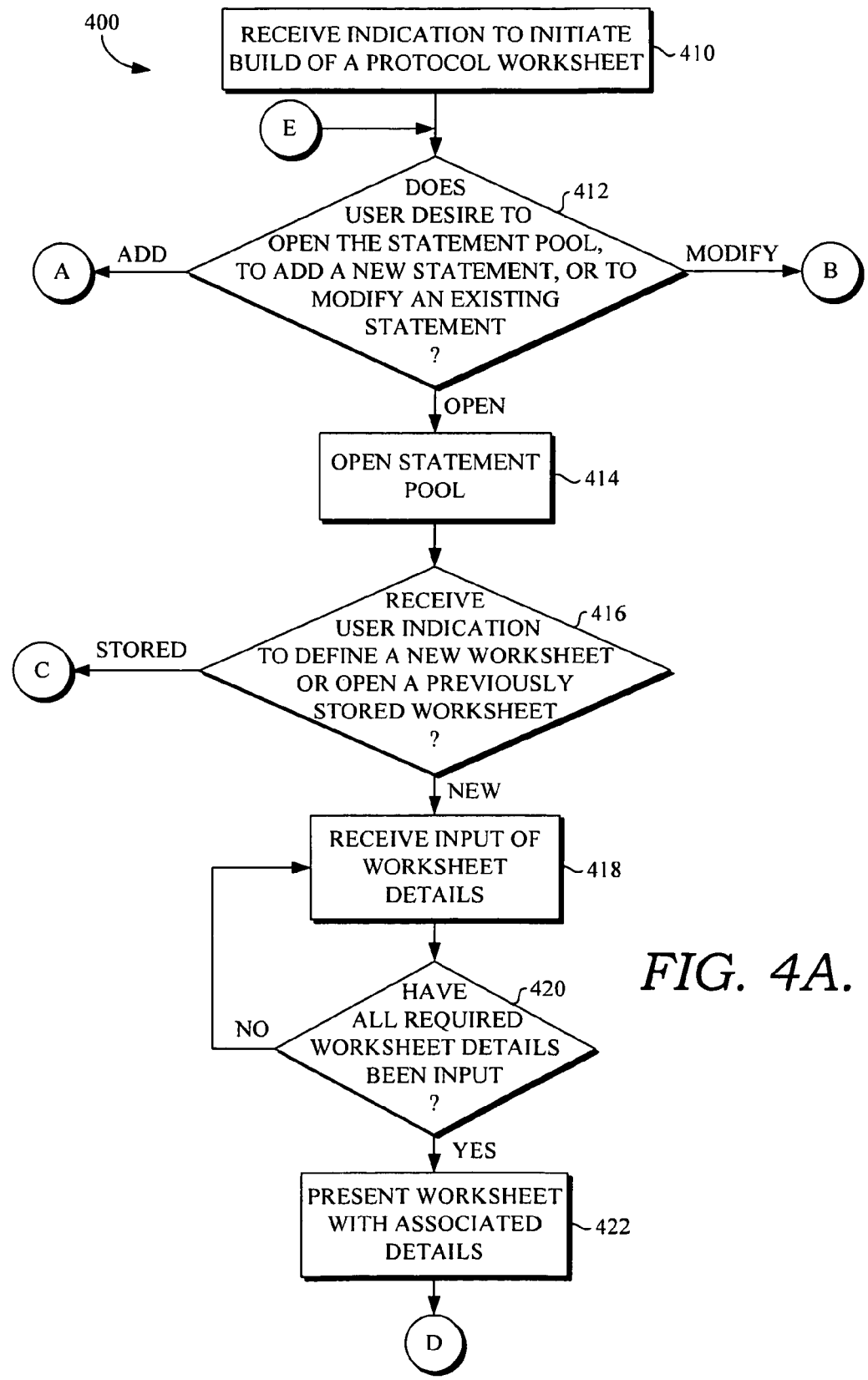
FIGS. 4A-4E are a flow diagram showing a method for building a protocol worksheet, in accordance with an embodiment of the present invention.
Figure 4B:
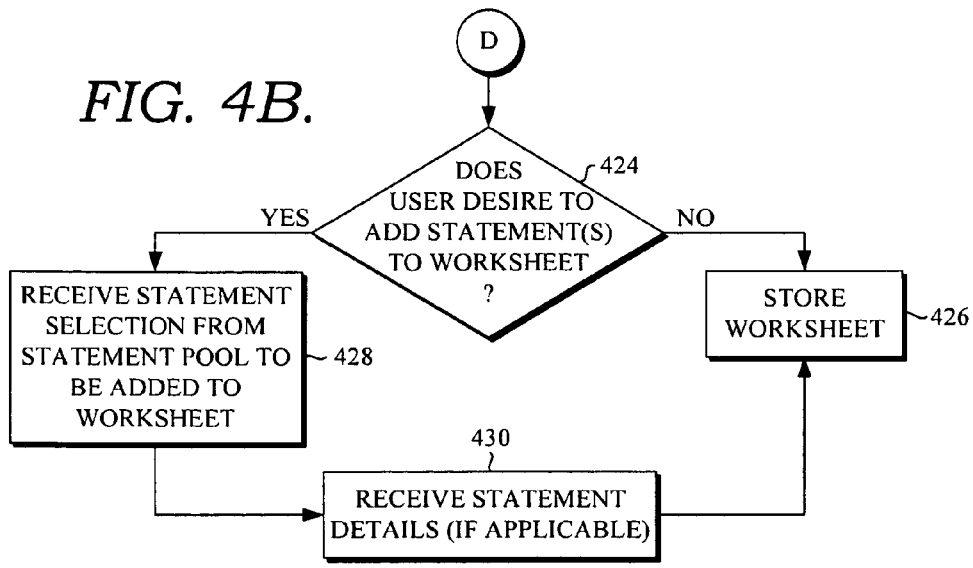
Figure 4C:
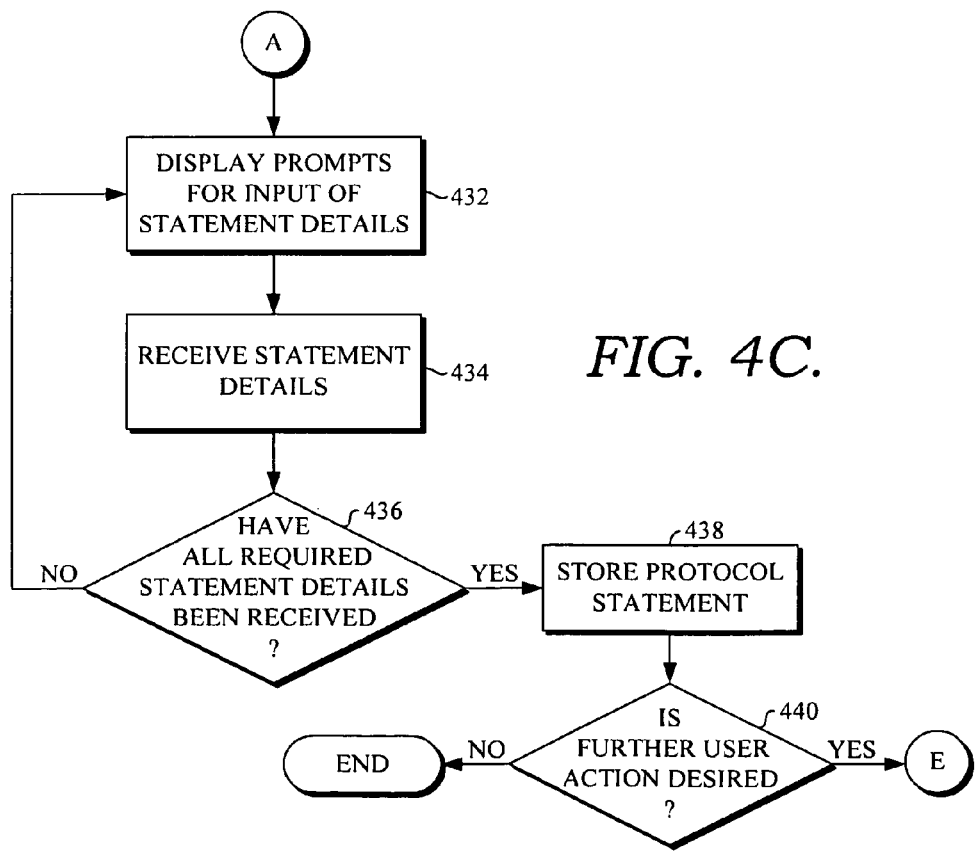
Figure 4D:
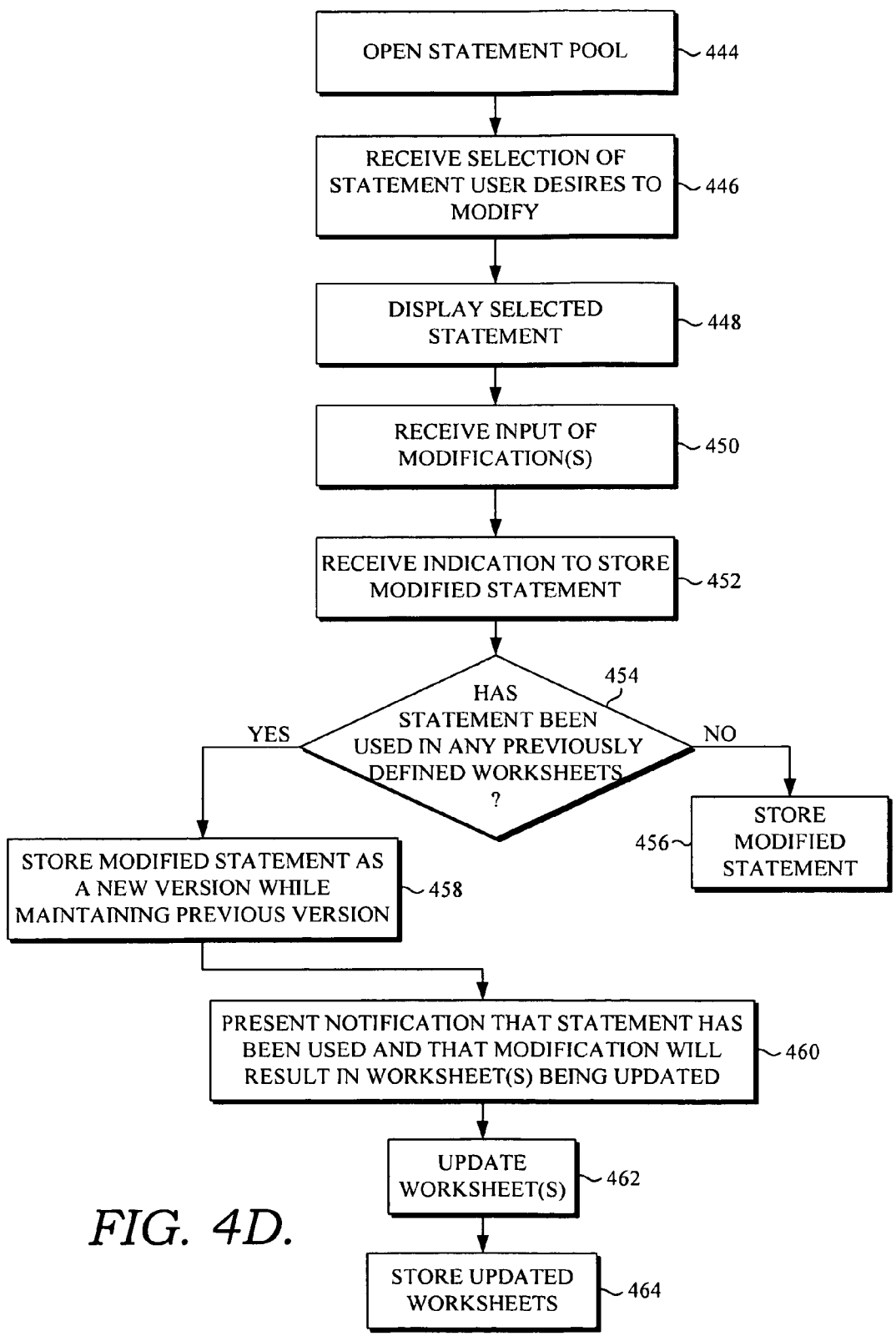
Figure 4E:
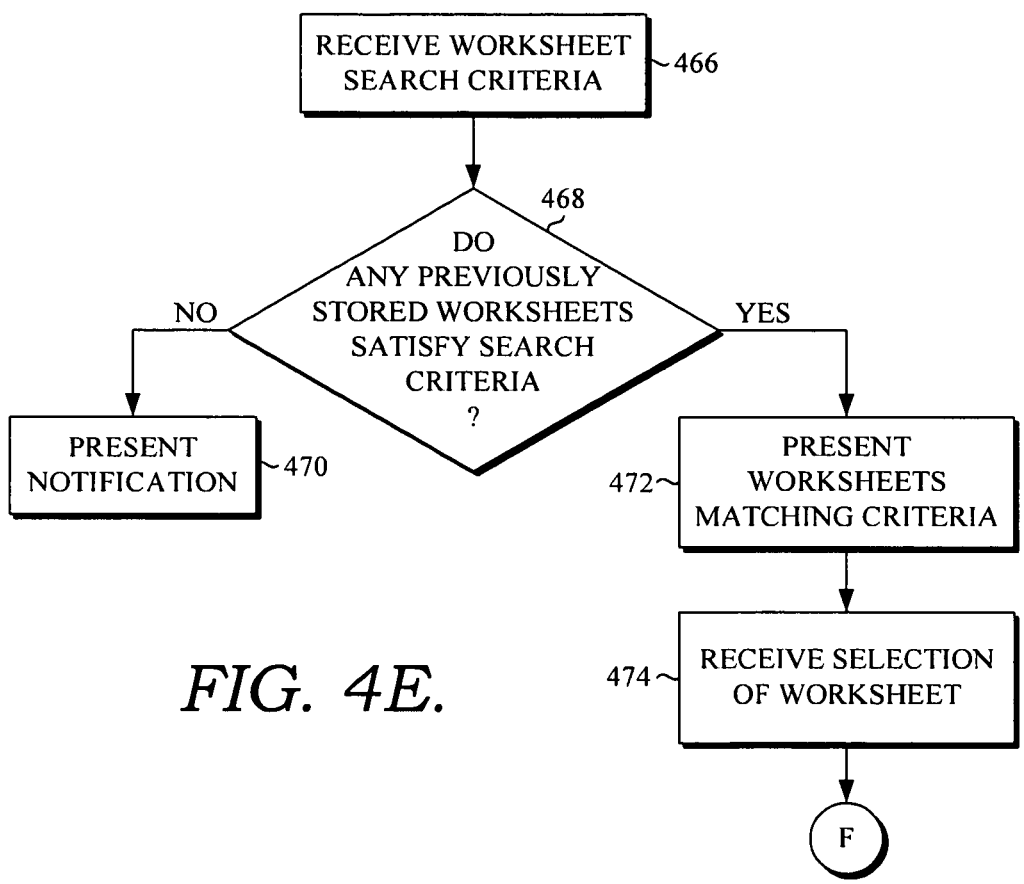
Figure 6A:
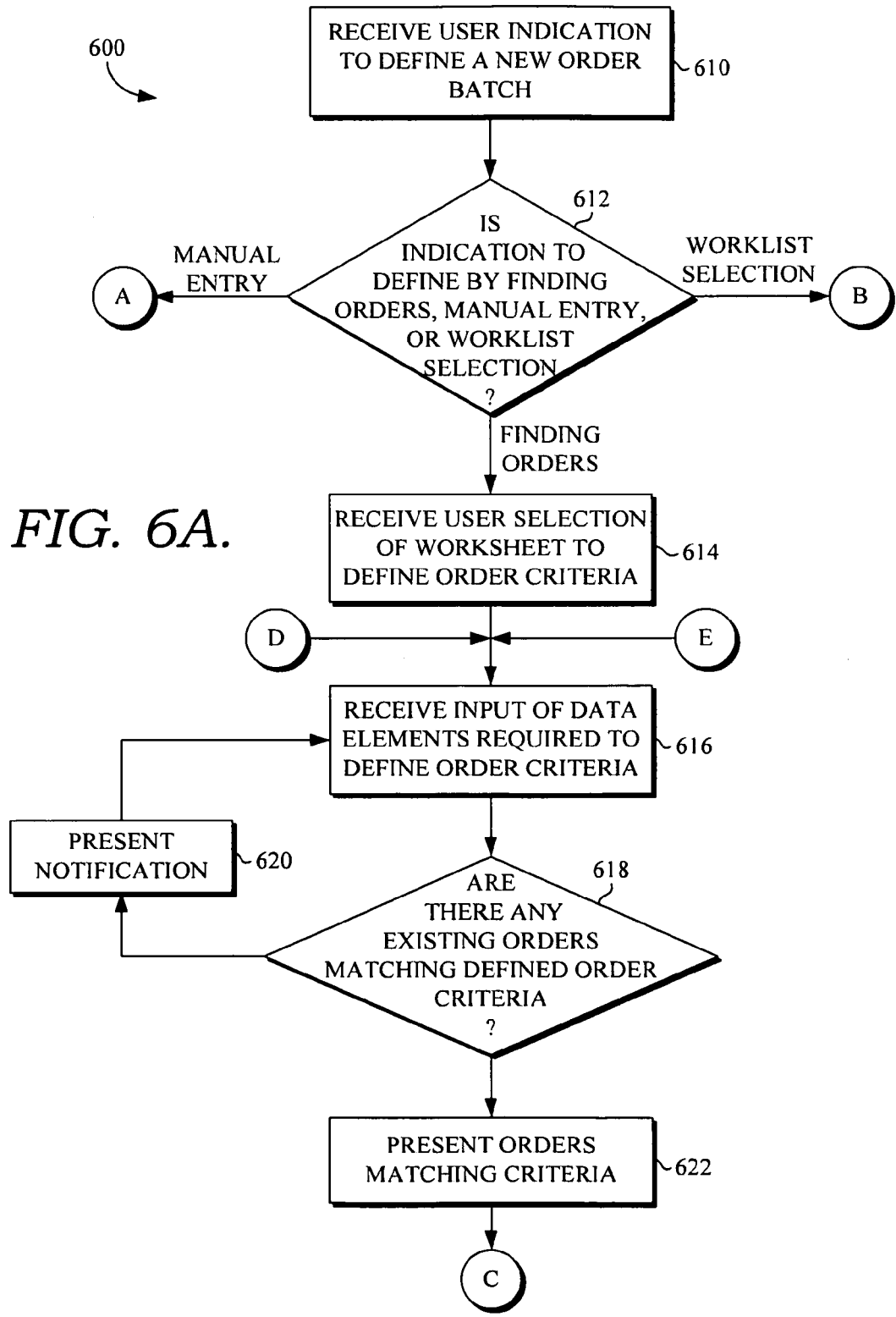
FIGS. 6A-6D are a flow diagram showing a method for defining a protocol batch, in accordance with an embodiment of the present invention.
Figure 6B:
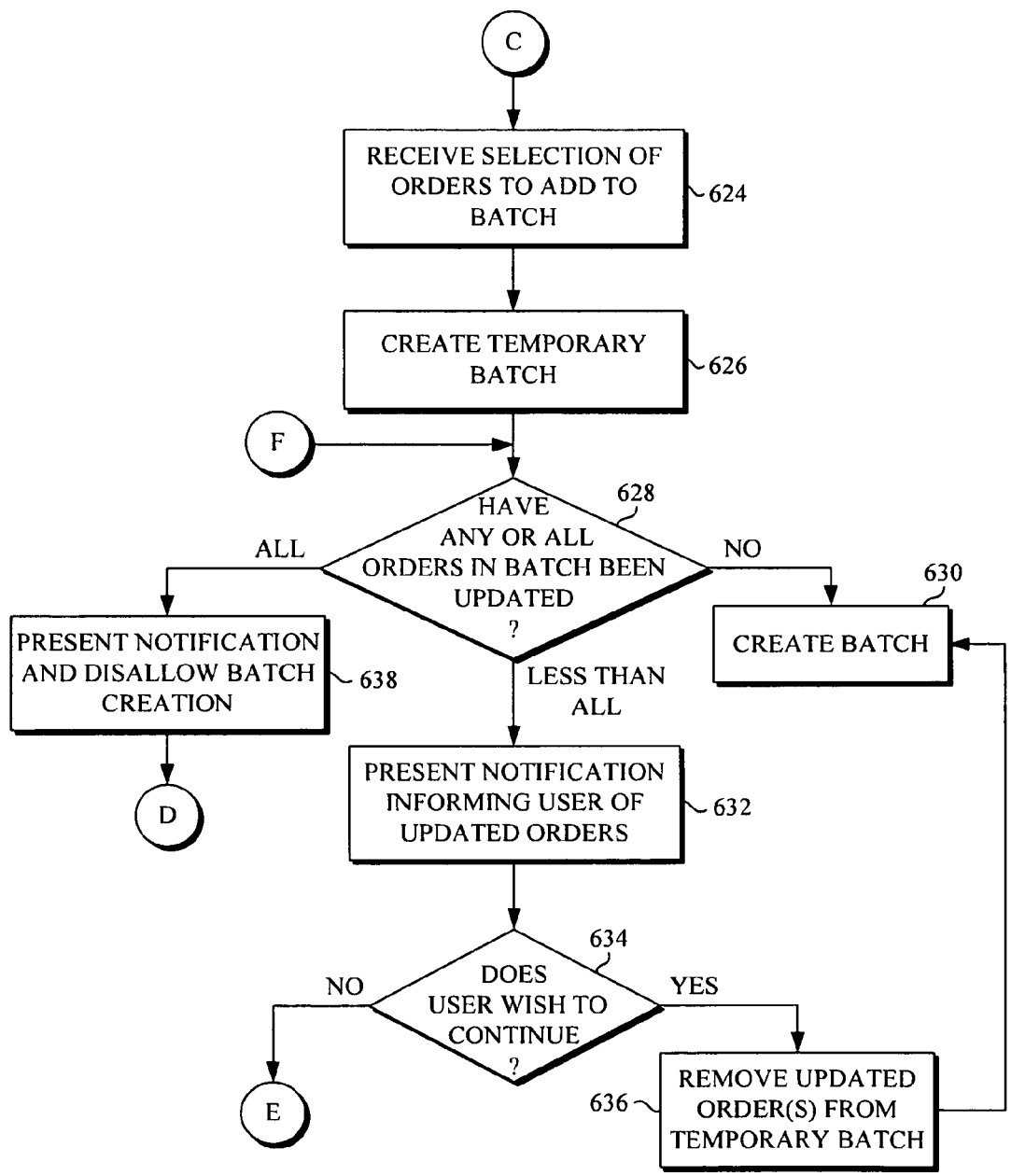
Figure 6C:
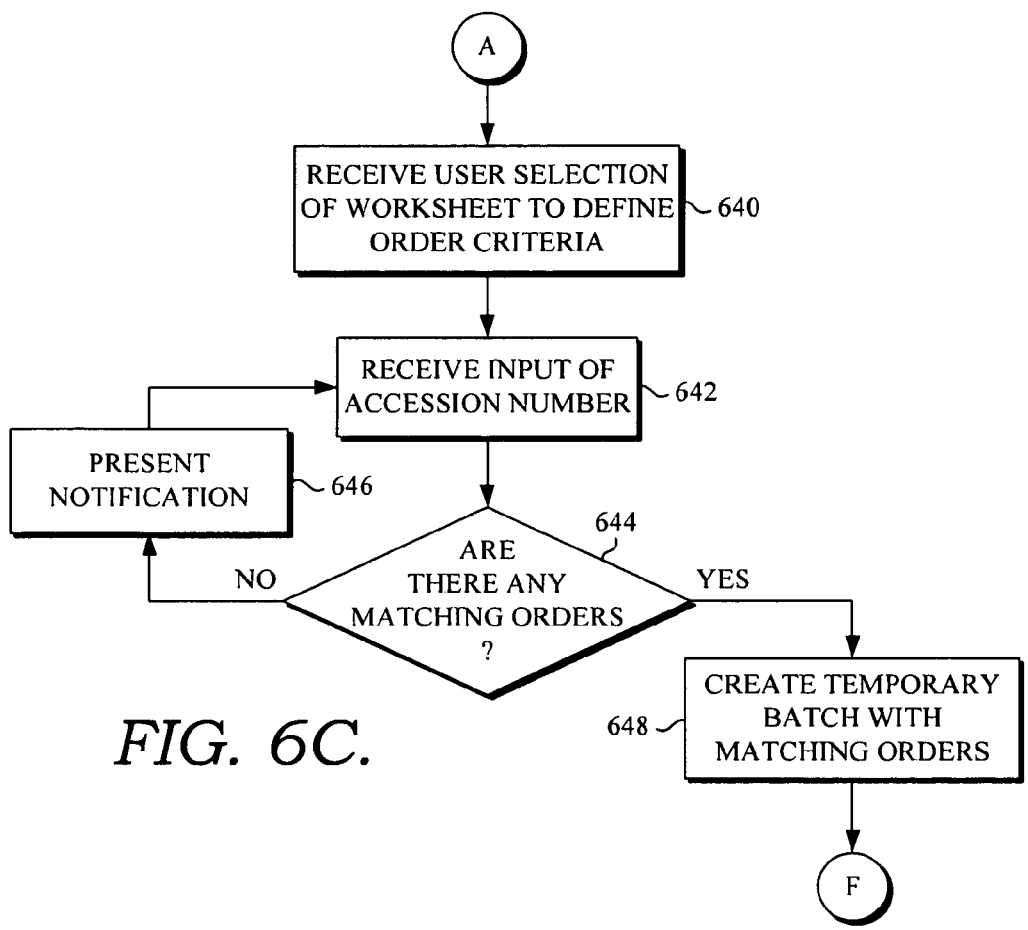
Figure 6D:
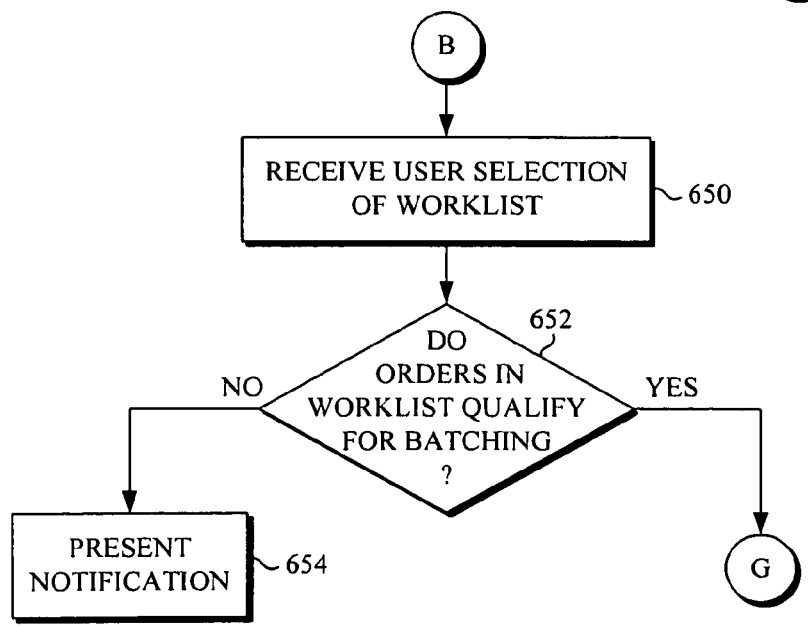

As previously mentioned, embodiments of the present invention relate to computerized methods and systems for use in, e.g., a molecular diagnostic laboratory environment, for creating and documenting protocol orders. With reference to FIG. 2, a block diagram illustrating how embodiments of the present invention alter the capture of information in the diagnostic laboratory environment is shown and designated generally as reference numeral 200. Absent the electronic creation and documentation of protocol orders disclosed herein, a clinician will typically place a clinical order for a diagnostic test result to be determined for a particular patient, as indicated at block 210. (The terms "individual", "person", and "patient" are used interchangeably herein and are not meant to limit the nature of the referenced individual in any way. Rather, the methods and systems described herein are equally applicable, for instance, in a veterinary setting. Further, use herein of the term "patient" is not meant to imply any particular relationship between the individual in question and those defining or building protocol worksheets, defining batches, initiating protocol orders, and the like.) Subsequently, the appropriate diagnostic test or tests necessary to determine the ordered result will be run and a discrete result will be captured, as indicated at block 212. If desired, a final report may then be generated summarizing the test findings, as indicated at block 214.

Utilizing this model, typically, the clinical order, the discrete result and the final report will be the only items of information electronically captured and stored in association with the patient's electronic medical record. All other information related to processing the specimen from collection to discrete test result, if documented at all, is documented manually in lab notebooks or the like.

Embodiments of the present invention alter this workflow by introducing protocol orders into the electronic documentation process, as shown at block 216. As utilized herein, the terms "protocol", "protocol order," and "workflow order" are interchangeable and refer to an order that intervenes between a clinician's order and a discrete, reportable result that allows a laboratory technologist to document steps that are taken with respect to a specimen. Protocol orders are defined by one or more protocol statements and associated with worksheets, as more fully described below. Documentation of information related to protocol orders electronically captures data associated with a case, not discrete patient results.

Worksheets are a collection of protocol statements that steps an actor (e.g., a laboratory technologist) through the completion of a protocol order, and optionally, the creation of a sample from a specimen or another sample, or the modification of an existing sample or specimen. Worksheets are configurable and can be customized to match the workflow needs of a particular diagnostic laboratory, no matter the complexity. Worksheets support the capture of different types of data including, but not limited to, numeric data, coded list data, text, calculations, dates, times, personnel identification, and check-boxes. Creation or building of protocol worksheets is more fully described below with reference to FIG. 4.

Protocol orders are associated with worksheets and are comprised of protocol statements representing any desired data element for which a value may be determined and documented. Protocol statements, like the worksheets into which they are incorporated, may be customized and defined to meet the needs of particular diagnostic laboratories. A protocol order can be associated with one and only one worksheet. A worksheet, however, can be associated with many protocol orders. For instance, a protocol order for Jane Doe may be associated with a DNA extraction worksheet. That particular protocol order cannot be associated with any other worksheet. However, the DNA extraction worksheet may be associated with another protocol order—a DNA extraction protocol order for John Smith, for instance.

By way of example only, and not limitation, protocol orders may be utilized to transform a collected specimen into one or more samples. Further, protocol orders may be utilized to create a plurality of containers from a particular specimen or sample. Still further, protocol orders may require input of the product of a prior protocol order. Thus, embodiments of the present invention support documentation, through protocol orders, of multiple generations of a specimen or sample.

Protocol orders and/or containers may be grouped together to form a batch. Batching of protocol orders and/or containers may be useful, for instance, where values for particular data elements may be common among a plurality of specimens or samples, for instance, the temperature of a run or the lot number of an enzyme. Accordingly, embodiments of the present invention support data capture by way of shared protocol statements, as more fully described below, such that a laboratory technologist, or the like, need only input the shared protocol statement value one time. Other information, for instance, DNA purity or concentration will be specific to a particular output sample or container. Thus, embodiments of the present invention further support data capture by way of protocol statements that are specific to a particular sample or specimen. A single worksheet may be designed to incorporate both shared and sample/specimen-specific protocol statements. Batching of protocol orders and/or containers is more fully described below with reference to FIG. 6.

In operation, though not shown in FIG. 2, once a clinician places an order for a particular diagnostic test result to be determined, a specimen is collected from the patient (e.g., whole blood, buccal swab, tumor tissue, amniotic fluid, or the like) and transported to the laboratory. A number of process-related steps may subsequently take place to generate the discrete result desired. For instance, the laboratory technologist may evaluate the specimen to determine if it is suitable for testing (e.g., based on volume, appearance, how it was transported, etc.). In accordance with embodiments of the present invention, if the specimen is determined to be suitable, such determination may be documented through use of a protocol order. Likewise, if the specimen is determined to be unsuitable, such determination may be documented through use of a protocol order as well.

If determined suitable for testing, the technologist may subsequently separate the specimen into a plurality of separate containers (which may be documented through a second-generation protocol order), moving one or more to a storage facility in the event further testing is deemed necessary and keeping one or more in the laboratory for testing. This is shown at block 218. The separation of containers, labeling, transporting, and the like may be documented through the use of protocol orders and stored in a general data repository and/or in association with the patient's electronic medical record.

A variety of process steps may then be performed on the container or containers maintained in the laboratory. By way of example only, it may be transformed into one or more samples (e.g., DNA, RNA, particular cell line isolations, and the like) through the use of protocol orders. A sample transformed from a specimen may subsequently be utilized to generate another sample through the use of another protocol, as indicated at block 220. For instance, an amniotic fluid sample may be transformed through the use of a first protocol into a DNA sample and the DNA sample may subsequently be transformed into an amplified PCR product sample through the use of a second protocol. Each of the specimen and sample(s), and the steps taken (and relevant surrounding conditions) to generate the specimen/sample may be documented through the use of protocols in accordance with embodiments of the present invention. Thus, embodiments of the present invention support and track documentation of multiple generations of a specimen and/or sample. Additionally, if a specimen or container(s) fails input validation (for instance, fails to meet volume requirements) and/or if a protocol order fails to generate a valid result (as more fully described below), it may be repeated and a note of its repetition may be documented in accordance with embodiments of the present invention.

Once all desired protocol orders have been completed with respect to a particular sample or specimen, a discrete result may be documented, as indicated at block 212. As all of the process-related steps or protocol orders were documented between collection of the specimen and generation of the result, a director, supervisor, or other authorized individual can easily review the result and approve or reject it, as indicated at block 222. The director, supervisor, or other individual may then generate a final report to summarize the findings and methods and make the report available to the clinician who placed the order at block 210. Again, as all of the process-related steps or protocol orders have been documented, the final report may also be reviewed for accuracy or audit, if desired. This is indicated at block 224.

Often times multiple clinical orders (226, 228) that may generate multiple discrete results (230, 232, respectively) may be received as part of a case. A "case," as the term is utilized herein, refers to a group of clinical orders that are related to a clinical scenario. Each of the clinical orders and results may be documented in association with the case, some of which may not utilize documentation of protocols (e.g., general laboratory or HLA orders may be part of a case as well). The use of protocol orders does not prohibit these results from being incorporated into the results report 214 as well.

It will be understood and appreciated by those of ordinary skill in the art that the particular examples described with reference to FIG. 2 are exemplary only and are not intended to limit the scope of the invention in any way. FIG. 2 is shown herein merely to illustrate that use of protocol orders and their related documentation alters the traditional diagnostic laboratory workflow.

Turning now to FIG. 3, an exemplary system suitable for use in implementing embodiments of the present invention is shown and designated generally as reference numeral 300. System 300 includes a validation engine 310, a worksheet-building engine 312, a proactive-notification engine 314, a user device 316, and a database 318, all in communication with one another through a network 320. The network 320 may include, without limitation, one or more local area networks (LANs) and/or wide area networks (WANs). Such networking environments are commonplace in offices, enterprise-wide computer networks, intranets, and the Internet. Accordingly, the network 320 is not further described herein.

The database 318 is configured to store information associated with at least one protocol order. In various embodiments, such information may include, without limitation, a protocol order name, one or more protocol statements defining required or desired data elements, one or more values associated with a protocol statement, and the like. In embodiments, the database 318 is configured to be searchable for one or more protocol statements and/or associated values stored in association therewith. It will be understood and appreciated by those of ordinary skill in the art that the information stored in the database 318 may be configurable and may include any information relevant to a protocol order and/or a case or patient associated therewith. The content and volume of such information are not intended to limit the scope of embodiments of the present invention in any way. Further, though illustrated as a single, independent component, database 318 may, in fact, be a plurality of databases, for instance, a database cluster, portions of which may reside on a computing device associated with the validation engine 310, the worksheet-building engine 312, the proactive-notification engine 314, the user device 316, another external computing device (not shown) and/or any combination thereof.

The validation engine 310 includes various components and is configured to operate utilizing at least a portion of the information stored in the database 318. The validation engine 310 includes a receiving component 322, a protocol order determining component 324, a value receiving component 326, an invalid value notification component 328, a sequence determining component 330, and an invalid sequence notification component 332. The receiving component 322 is configured to receive an indication that a patient specimen has been collected and/or an indication of at least one result that is to be generated from the patient specimen. That is, the receiving component 322 is configured to receive an indication that a specimen has been collected, the nature of the specimen (e.g., the source of the specimen), and at least one clinical order associated with collection of the specimen.

The protocol order determining component 324 is configured to determine one or more protocol orders for which a value must be received for the ordered clinical result(s) to be generated from the patient specimen. Typically, protocol orders will be defined by a user, through a worksheet building process as more fully described below with reference to FIG. 4, and stored in database 318. A protocol order name or other identifier is typically assigned to the protocol order and stored in association therewith. Thus, the protocol order determining component may permit a user to input a protocol order name (or other identifier) which will subsequently be utilized to search the database 318 for the desired protocol order worksheet. The protocol order worksheet will then be presented to the user.

Often, completion of multiple protocol orders is necessary for the desired clinical result(s) to be generated. Accordingly, a plurality of protocol order worksheets may be grouped or batched together and the batch may be identified by a particular identifier. The plurality of protocol order worksheets may then be retrieved by the protocol order determining component upon input of the batch identifier. The protocol order worksheets may then be displayed in the sequence necessary for accurate generation of the desired clinical result(s).

The value receiving component 326 is configured to receive a value for each protocol statement on a worksheet for which a value is required or desired for the ordered clinical result(s) to be generated from the patient specimen. The value receiving component 326 is further configured to determine if a received value satisfies a pre-defined value threshold. The pre-defined value threshold may include a minimum value, a maximum value, a value range, or any combination thereof.

The invalid value notification component 328 is configured to present an invalid value notification or alert if a value received in association with a protocol statement fails to satisfy the pre-defined value threshold. The invalid value notification component 328 is further configured to present an invalid value notification or alert if a value is required for a particular protocol statement and no value is input therefore. In accordance with embodiments of the present invention, if all protocol statements associated with a presented worksheet for which a value is required are not associated with a valid value, the user may be prevented from accessing subsequent protocol worksheets or reporting results. A notification that the user will not be permitted to proceed through a sequence of protocol worksheets or report results until valid values are received for all required protocol statements may be generated by the invalid value notification component 328. If desired, a user with appropriate authorization may be permitted to override the inability to proceed, forcing the validation engine 310 to accept the invalid or absent value.

The sequence determining component 330 is configured to determine if a value for a first of a plurality of protocol statements must be received prior to input of a second of the plurality of protocol statements. Similarly, the sequence determining component 330 is configured to determine if a first protocol worksheet must be completed prior to initiation of a second protocol worksheet. The invalid sequence notification component 332 is configured to present an invalid sequence notification if it is determined that input related to the second of the plurality of protocol statements has been attempted prior to the value for the first of the plurality of protocol orders being received or if initiation of a second protocol worksheet is attempted prior to completion of a first protocol worksheet.

The worksheet-building engine 312 includes a protocol statement receiving component 334, a batch-defining component 336, a statement value receiving component 338, an associating component 340, a searching component 342, and a presentation component 344. The protocol statement receiving component 334 is configured to receive a plurality of protocol statements that define a protocol order which is associated with the worksheet being built or defined. The protocol statement receiving component 334 is configured to receive protocol statements that are either specific to a particular sample or specimen associated with the protocol order or protocol statements that are to be shared among members of a batch of protocol orders or containers such that a value associated with such shared protocol statements need only be input one time instead of once for each member of the batch.

The batch-defining component 336 is configured to associate two or more protocol orders or containers with one another in a batch. As previously discussed, batching orders or containers together permits entry of values associated with shared protocol statements a single time rather than once for each of the batched protocol orders or containers. Batching of protocol orders also permits a sequence of protocol orders that are necessary to generate a particular result to be identified as a group and the worksheets associated therewith to be accessed sequentially, with invalid or incomplete prior protocol orders preventing access to subsequent protocol orders.

The statement value receiving component 338 is configured to receive input of a value associated with each of the protocol statements comprising a protocol order. The statement value receiving component 338 is configured to receive values for both specimen or sample specific protocol statements and shared protocol statements.

The associating component 340 is configured to automatically associate a value received for each protocol statement with the protocol order to which it pertains. The associating component 340 is further configured to automatically associate values for shared protocol statements with each of the plurality of protocol orders or containers pertaining thereto.

The searching component 342 is configured to search at least one data store (e.g., database 318) for protocol orders that satisfy user-defined criteria. That is, upon receiving input of an identifier associated with a protocol order or batch of protocol orders, e.g., a name assigned thereto, the searching component 342 is configured to search the database 318 and retrieve all protocol orders matching the input criteria.

The presentation component 344 is configured to present the worksheet(s) associated with retrieved protocol orders. Upon receiving input of one or more values associated with a protocol statement or statements associated with a retrieved worksheet, the presentation component 344 is further configured to present the input value(s), as well as the result of any calculation that may be associated therewith.

The proactive-notification engine 314 includes a changed statement value receiving component 346, a versioning component 348, a determining component 350, and a notification generating component 352. The changed statement value receiving component 346 is configured to receive input of a changed value associated with a protocol statement for which a prior value was stored. For instance, if a 260/280 DNA purity value of 1.7 had been input on a DNA extraction worksheet for a protocol order associated with a clinical order for a gene mutation test for Jane Doe and it is subsequently discovered that the DNA purity value should have been 1.8, the changed statement value receiving component 346 is configured to accept the changed statement value. Additionally, the changed statement value receiving component 346 may be configured to receive input of changed protocol statements associated with protocol order worksheets. Any and all such variations, and any combinations thereof, are contemplated to be within the scope of embodiments of the present invention.

In the event a protocol statement or statement value is changed, the versioning component 348 is configured to receive notification of such change from the changed statement value receiving component and to assign a version indicator including at least one time associated therewith to each of a prior statement or statement value and the changed statement or statement value. The assigned version indicator is stored in association with the respective statement or statement value in a data store (e.g., database 318).

In the event a protocol statement or statement value is changed, the determining component 350 is configured to determine if a second protocol order, protocol statement, and/or reported result is affected by the changed value or statement. The notification generating component 352 is configured to generate a notification if it is determined that a second protocol order, protocol statement, and/or result is affected by the changed value. Upon receiving such notification, a user may determine whether further corrective action is necessary to facilitate accurate documentation and reporting.

As previously mentioned, the system 300 further includes a user device 316 in communication with the database 318, the validation engine 310, the worksheet-building engine 312, and the proactive-notification engine 314 via the network 320. The user device 316 may be associated with any type of computing device, such as computing device 100 described with reference to FIG. 1, for example. Though not shown in FIG. 3, the user device 316 typically includes at least one presentation module configured to present (e.g. display) one or more worksheets and/or results associated with a specimen or sample. In this regard, the presentation module may be configured to receive protocol worksheets, for instance, from database 318, and utilize such protocol worksheets to receive input of required protocol statement values. The presentation module associated with the user device 316 may be further configured to receive worksheet build templates, for instance, from database 318, and utilize such templates to receive input of desired protocol statements to define a protocol order. Such embodiments are more fully described herein below.

It will be understood and appreciated by those of ordinary skill in the art that other components not shown may also be included with the system 300. Further, additional components not shown may also be included within any of the database 318, the validation engine 310, the worksheet-building engine 312, the proactive-notification engine 314, and the user device 316. Additionally, any components illustrated in FIG. 3 in association with the validation engine 310, the worksheet-building engine 312, or the proactive-notification engine 314 may additionally or alternatively be associated with any of the other illustrated engines, the user device 316, and/or another external computing device, e.g., a server (not shown). Any and all such variations are contemplated to be within the scope of embodiments hereof.

Turning now to FIG. 4, a flow diagram showing a method for building a protocol worksheet, in accordance with an embodiment of the present invention, is illustrated and designated generally as reference numeral 400. Method 400 may be implemented on the above-described exemplary computing system environment (FIG. 1) and, by way of example only, may be utilized by a laboratory technologist to define a protocol order worksheet for documenting process-related information.

Initially, as indicated at block 410, an indication to initiate build of a protocol worksheet is received. Subsequently, as indicated at block 412, it is determined if the user desires to open a protocol statement pool (i.e., a pool of protocol statements that have either been provided as starter content or previously input by a user), to add a new protocol statement, or to modify an existing protocol statement. If it is determined that the user desires to open the protocol statement pool, the protocol statement pool is subsequently opened, as indicated at block 414.

Next, it is determined whether the user desires to define a new worksheet or to open a previously stored worksheet. This is indicated at block 416. If it is determined that the user desires to define a new worksheet, input of the worksheet details (e.g., worksheet name, author, etc.) are subsequently received, as indicated at block 418. Once the worksheet details have been received, it is determined whether all required worksheet details have been received. This is indicated at block 420. If it is determined that all required worksheet details have not been received, the user is returned to the step indicated at block 418 and prompted for additional worksheet details. If, however, it is determined at block 420 that all required worksheet details have been received, the worksheet is presented (e.g., displayed) in association with the associated details. This is indicated at block 422.

Subsequently, as indicated at block 424, it is determined whether or not the user desires to add one or more protocol statements to the worksheet. If it is determined that the user does not desire to add any protocol statements to the worksheet, the worksheet is stored, as indicated at block 426. If, however, it is determined at block 424 that the user does desire to add one or more protocol statements to the worksheet, a selection is received from the protocol statement pool of one or more protocol statements the user desires to add to the worksheet. This is indicated at block 428. Next, if desired, the user may input protocol statement details or notes, as indicated at block 430. Once all protocol statements and their respective details, if applicable, are added to the worksheet, the worksheet is stored, for instance, in association with database 318 of FIG. 3, as indicated at block 426.

Returning now to block 412, if it is determined that the user desires to add a new protocol statement, prompts are presented (e.g., displayed) for input of the new protocol statement details. This is indicated at block 432. Next, the protocol statement details are received, as indicated at block 434. It is subsequently determined, as indicated at block 436, whether or not all required protocol statement details have been received. If it is determined at block 436 that all required protocol statement details have not been received, the user is again prompted for input of the protocol statement details, as indicated at block 432. If, however, it is determined at block 436 that all required protocol statement details have been received, the new protocol statement is stored in association with the worksheet, as indicated at block 438. If desired, the new protocol statement may also be stored in association with the protocol statement pool. Subsequently, it is determined if further user action is desired, as indicated at block 440. If no further user action is desired, the method ends, as indicated at block 442. If, however, it is determined that further user action is desired, the method returns to the step indicated at block 412 and it is determined what action the user desires to perform.

Again returning to block 412, if it is determined that the user desires to modify an existing protocol statement, the protocol statement pool is opened, as indicated at block 444, and presented to the user. Subsequently, as indicated at block 446, a selection of a protocol statement from the protocol statement pool that the user desires to modify is received and such protocol statement is presented (e.g., displayed) to the user, as indicated at block 448. Next, input indicative of the desired modification(s) to the protocol statement is received, as indicated at block 450. When all desired modifications have been input, an indication to store the modified protocol statement, e.g., in association with database 318 of FIG. 3, is received. This is indicated at block 452.

Subsequently, as indicated at block 454, it is determined whether or not the modified protocol statement has been used in any previously defined worksheets. If it is determined that the modified protocol statement has not been used in any previously defined worksheets, the modified protocol statement is stored as indicated at block 456. If desired, the previous protocol statement and the modified protocol statement may each be assigned a version identifier (and at least one time associated therewith) and, while the modified version will be utilized, the previous version may be archived.

If, however, it is determined at block 454 that the newly modified protocol statement has been used in at least one previously defined worksheet, the modified protocol statement is stored as a new version while maintaining the prior version as well. This is indicated at block 458. Subsequently, notification is presented to the user that the newly modified protocol statement, in its prior form, has been used in at least one previously defined worksheet and that the modification will result in such previously defined worksheet(s) being updated. This is indicated at block 460. Absent receipt of an objection by the user, the previously defined worksheet(s) are subsequently updated, as indicated at block 462, and stored, e.g., in database 318 of FIG. 3, as indicated at block 464. Again, if desired, versions may be created and stored for archiving purposes.

Returning now to the step indicated at block 416, if it is determined that the user desires to open a previously stored worksheet rather than defining a new worksheet, user-defined worksheet search criteria are subsequently received, as indicated at block 466. Next, it is determined if any previously stored worksheets satisfy the user-defined worksheet search criteria. This is indicated at block 468. If it is determined that no previously stored worksheets satisfy the user-defined worksheet search criteria, a notification of such is presented to the user, as indicated at block 470. If, however, it is determined that one or more previously stored worksheets satisfy the search criteria, such worksheets (or a listing of the titles thereof) are presented, as indicated at block 472. Subsequently, as indicated at block 474, user selection of the desired worksheet is received, and the worksheet and its associated details are presented, as indicated at block 422. The method then proceeds as previously described.

Figure 5:
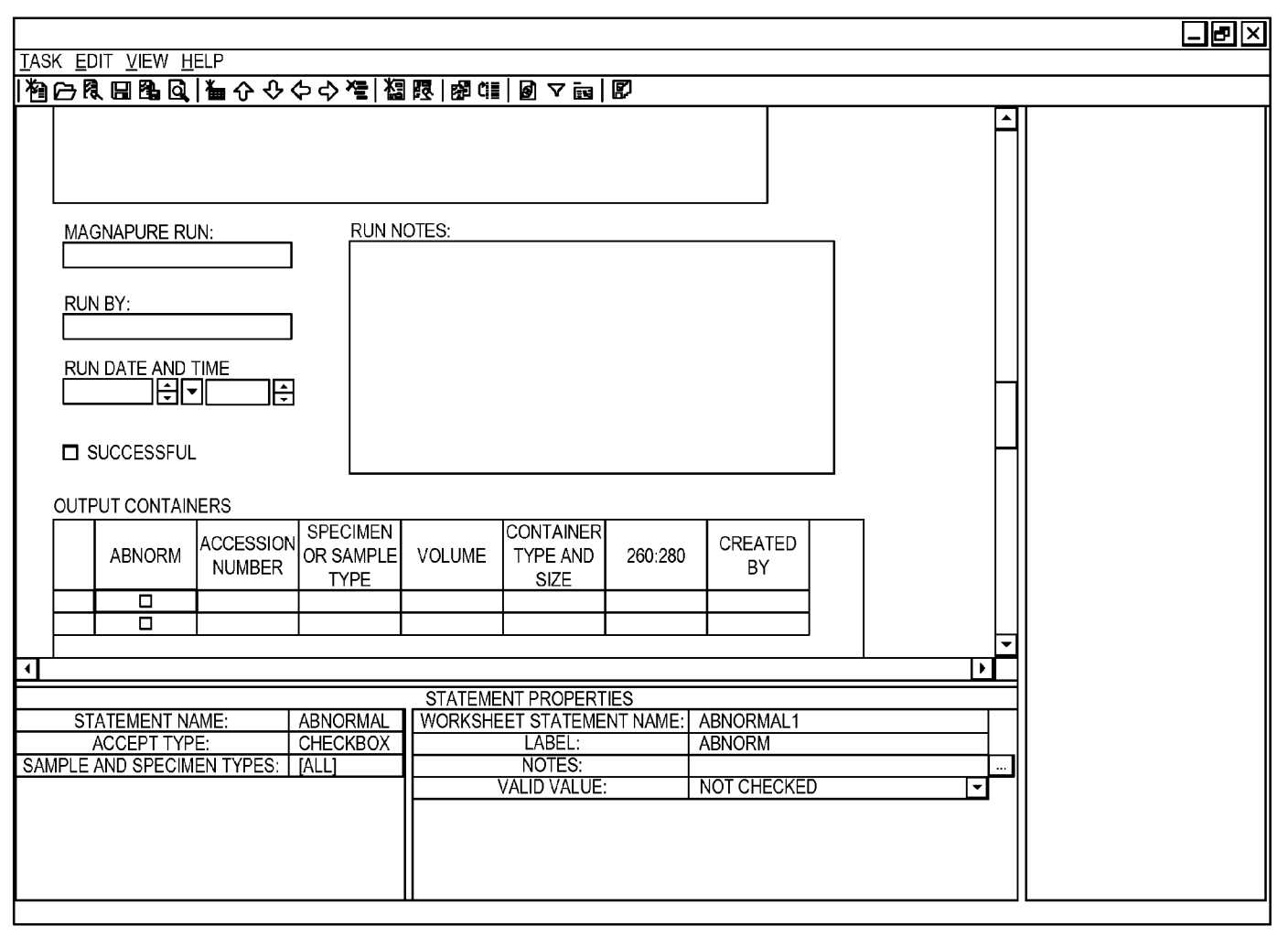

With reference to FIG. 5, an illustrative screen display of an exemplary user interface for building a protocol worksheet, in accordance with an embodiment of the present invention, is shown and designated generally as reference numeral 500. Screen display 500 includes a protocol statement defining area 502, a defined protocol statement properties area 504, and a run notes area 506. The protocol statement defining area 502 is configured to permit a user to input protocol order specific protocol statements and shared protocol statements, the difference between the two being visually denoted, for instance, by a different colored field background or the like. The protocol statement defining area 502 may additionally indicate, for instance by an asterisk next to the protocol statement or the like, that a value for a particular protocol statement is required. Any and all such variations are contemplated to be within the scope hereof.

The defined protocol statement properties area 504 is configured to present, e.g., display, any properties the user desires to input with respect to the particular protocol statement. The run notes area 506 is configured to permit the user to input any other details s/he desires to be associated with the protocol order worksheet. Between the defined protocol statement properties area 504 and the run notes area 506, a user building the worksheet 500 can effectively create an on-line procedure manual for completion of the associated protocol order.

Turning now to FIG. 6, a flow diagram showing a method for defining a protocol order batch, in accordance with an embodiment of the present invention, is illustrated and designated generally as reference numeral 600. Method 600 may be implemented on the above-described exemplary computing system environment (FIG. 1) and, by way of example only, may be utilized by a laboratory technologist to define a protocol order batch for documenting process-related information.

Initially, as indicated at block 610, a user indication to define a new protocol batch is received. Subsequently, it is determined whether the user is requesting to define the batch by locating existing protocol orders, by manual entry, or by worklist selection. This is indicated at block 612. If it is determined that the user is requesting to define the batch by locating existing protocol orders, user selection of a protocol worksheet to define protocol order criteria is subsequently received, as indicated at block 614. Subsequently, as indicated at block 616, input of data elements required to define the desired protocol order criteria is received.

Next, it is determined whether or not any existing protocol orders satisfying the defined protocol order criteria are stored in a database, e.g., database 318 of FIG. 3, as indicated at block 618. If it is determined that no existing protocol orders satisfy the defined protocol order criteria, notification of such is presented to the user, as indicated at block 620, and the user is returned to the step indicated at block 616. If, however, it is determined at block 618 that at least one existing protocol order satisfies the defined protocol order criteria, the matching protocol order(s) is presented to the user, as indicated at block 622. Subsequently, selection of which protocol order(s) to add to the batch is received, as indicated at block 624, and a temporary batch is created, as indicated at block 626.

Subsequently, it is determined whether any or all of the protocol orders in the batch have been updated. This is indicated at block 628. If it is determined that no protocol orders in the batch have been updated, the batch is created, as indicated at block 630. If, however, it is determined that some, but not all, of the protocol orders in the batch have been updated, notification informing the user of the updated protocol orders is presented, as indicated at block 632. The user is subsequently provided with the option to continue, as indicated at block 634. If the user opts not to continue, the user is returned to the step indicated at block 616. If, however, it is determined at block 634 that the user does wish to continue, the updated protocol order(s) is removed from the temporary batch, as indicated at block 636, and the batch is created, as indicated at block 630.

If it is determined at block 628 that all of the protocol orders in the batch have been updated, notification of such is presented to the user and creation of a batch including any of the updated protocol orders is disallowed. This is indicated at block 638. Subsequent to presentation of such notification, the user is returned to the step indicated at block 616.

Returning now to the step indicated at block 612, if it is determined that the user desires to define a new batch by manual entry, e.g., bar-code or keyboard entry of accession numbers, user selection of a worksheet to define protocol order criteria is received, as indicated at block 640. Next, user input of a value for at least one value, for instance, accession number, is received, as indicated at block 642. It is subsequently determined whether there are any protocol orders that match the input value(s). This is indicated at block 644. If it is determined that no orders match the input value(s), the user is presented with notification of such, as indicated at block 646, and returned to the step indicated at block 642.

If, however, it is determined at block 644 that one or more protocol orders match the input value(s), a temporary batch is created that contains the matching protocol order(s). This is indicated at block 648. Subsequently, the user is returned to the step indicated at block 628 and it is determined if any of the protocol orders in the batch have been updated.

Again returning to the step indicated at block 612, if it is determined that the user desires to define a new batch by worklist selection, user selection of the desired worklist is subsequently received, as indicated at block 650. Next, as indicated at block 652, it is determined whether any of the protocol orders in the worklist qualify for batching. If it is determined that none of the protocol orders qualify for batching, notification of such is presented to the user, as indicated at block 654. If, however, it is determined at block 652 that one or more protocol orders in the worklist qualify for batching, the user is returned to the step indicated at block 614 and user selection of a worksheet to define protocol order criteria is received.

Figure 7:
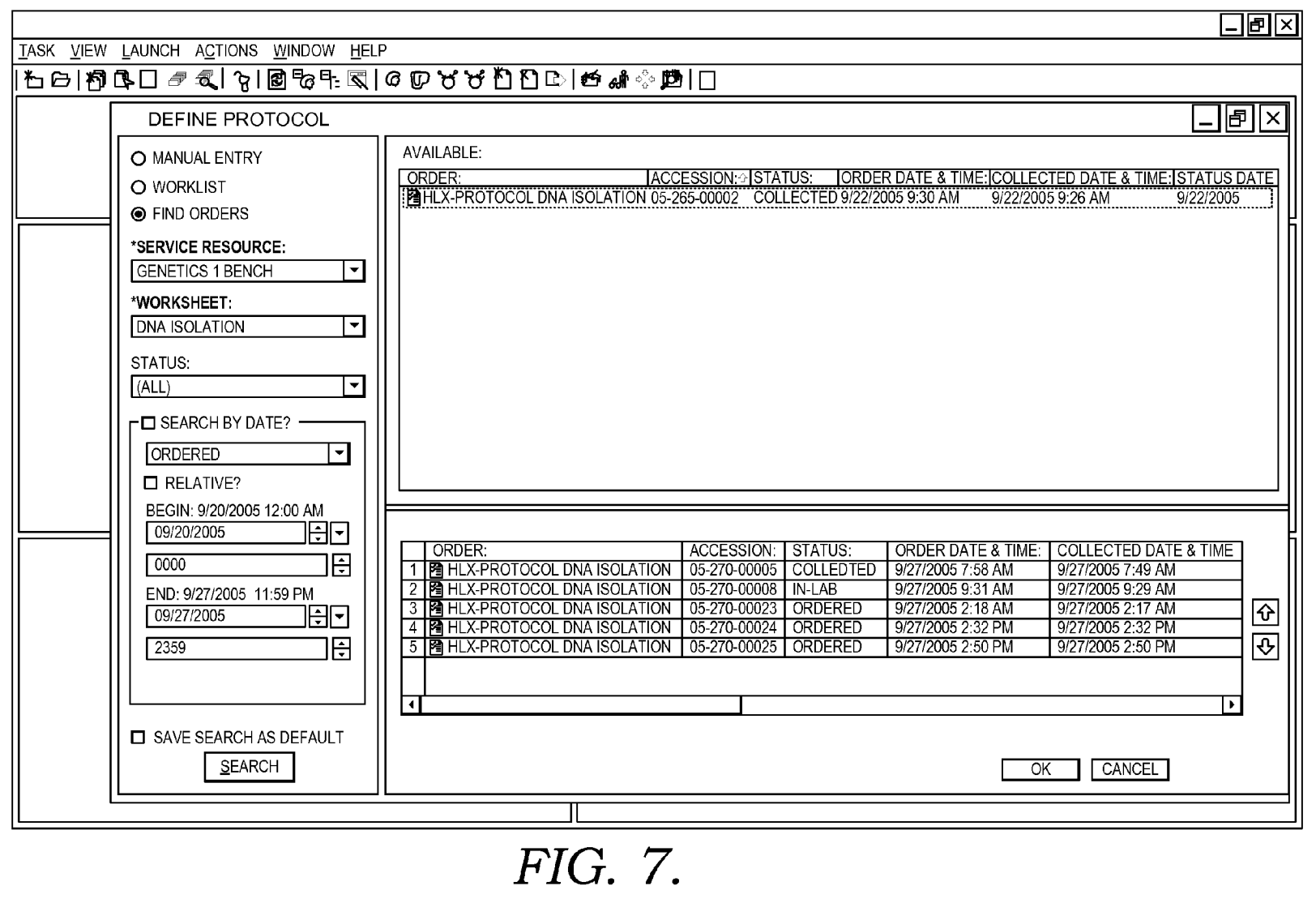

With reference to FIG. 7, an illustrative screen display of an exemplary user interface for defining a protocol order batch, in accordance with an embodiment of the present invention, is shown and designated generally as reference numeral 700. Screen display 700 includes a defining mode selection area 702, a protocol order criteria input area 704, an available, matching protocol order display area 706, and a selected protocol order display area 708.

The defining mode selection area 702 is configured to permit a user to selectively define a batch by manual entry, worklist selection, or location of existing orders. The protocol order criteria input area 704 is configured to permit a user to input a number of protocol order criteria, for instance, if the user has selected to define a batch by location of existing orders. The available, matching protocol order display area 706 is configured to present (e.g., display) all protocol orders matching criteria input by the user. The selected protocol order display area 708 is configured to present (e.g., display) those orders from the available orders that the user has selected to add to the defined batch. In one embodiment, a user may select and drag a protocol order from the available, matching protocol order display area 706 to the selected protocol order display area 708 if it is determined that adding of that protocol order to the batch is desired. Once a protocol order has been dragged to the selected protocol order display area 708, it is no longer displayed in the available, matching protocol order display area 706.

Figure 8:
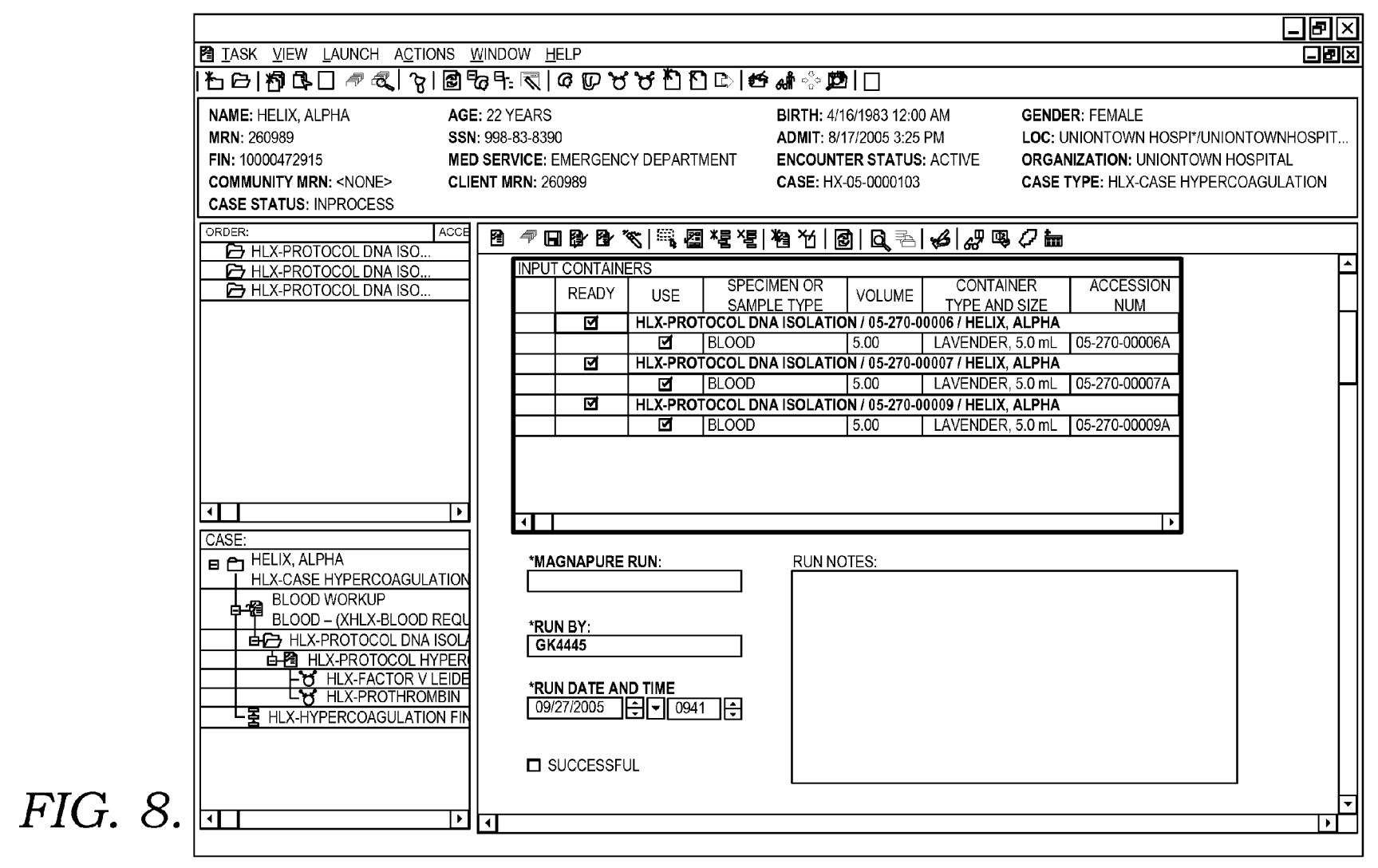

Turning now to FIG. 8, an illustrative screen display of an exemplary user interface for viewing information related to members of a protocol order batch, in accordance with an embodiment of the present invention, is shown and designated generally as reference numeral 800. In the view of FIG. 8, not only is information related to members of a protocol order batch shown in batch display area 802, details specific to a selected order are shown in detail display area 804, as is information pertaining to the case being worked-up in case detail display area 806.

Figure 9A:
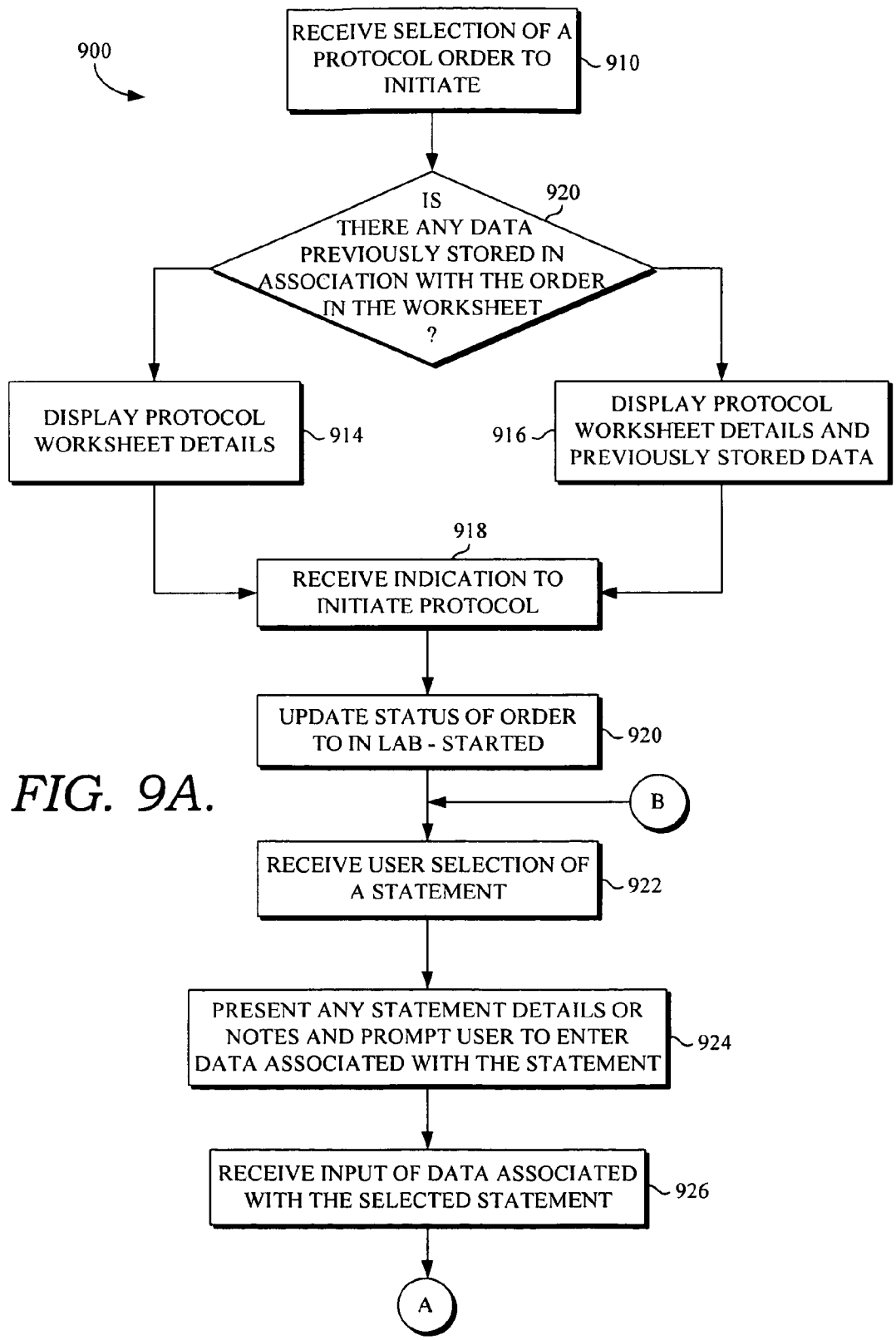
FIGS. 9A and 9B are a flow diagram showing a method for initiating a protocol, in accordance with an embodiment of the present invention.
Figure 9B:
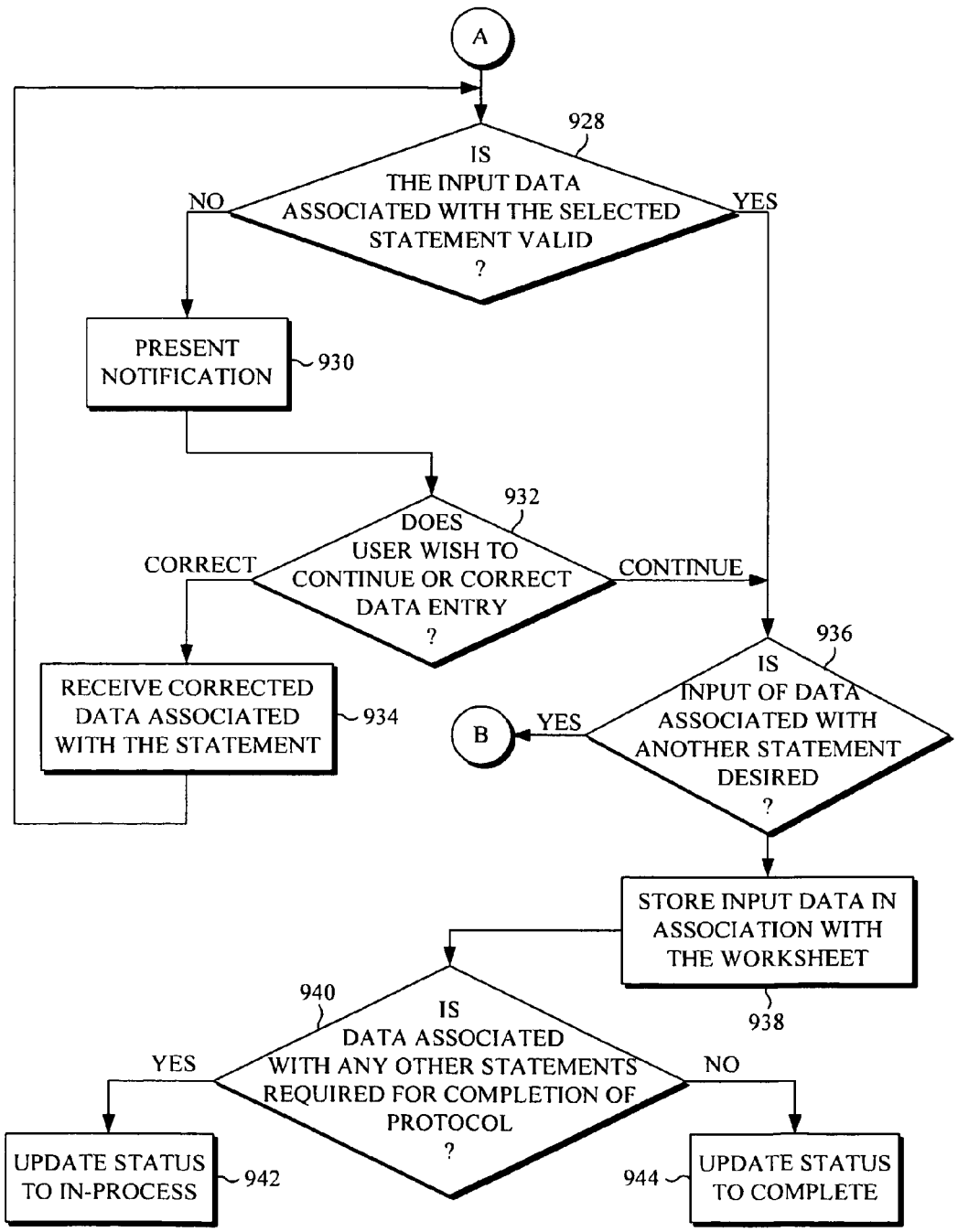

Turning now to FIG. 9, a flow diagram showing a method for initiating a protocol order, in accordance with an embodiment of the present invention, is illustrated and designated generally as reference numeral 900. Method 900 may be implemented on the above-described exemplary computing system environment (FIG. 1) and, by way of example only, may be utilized by a laboratory technologist to initiate a protocol order for documenting process-related information.

Initially, as indicated at block 910, a user indication of a protocol order to initiate is received. Subsequently, as indicated at block 912, it is determined whether there are any protocol statement values previously stored in association with the protocol order. If it is determined that no previously stored protocol statement values exist in association with the protocol order, the protocol worksheet details are presented (e.g., displayed), as indicated at block 914. If, however, it is determined at block 912 that one or more protocol statement values have been previously stored in association with the protocol order, the protocol worksheet details and previously stored value(s) are presented (e.g., displayed), as indicated at block 916.

Once the worksheet details (and previously stored value(s), if applicable) have been presented, an indication to initiate the protocol order is received, as indicated at block 918. Upon receiving such indication, the status of the protocol order is updated, for instance, to "In Lab—Started". It will be understood and appreciated by those of ordinary skill in the art that embodiments of the present invention are not limited to any particular status indicators and that any message or indicator that signals a user that the protocol order has been initiated is within the scope of embodiments hereof.

Next, as indicated at block 922, user selection of a particular protocol statement within the worksheet is received. Any details or notes stored in association with the protocol statement are subsequently presented and the user is prompted to enter a value for the protocol statement. This is indicated at block 924. Input of the value(s) associated with the selected protocol statement is subsequently received, as indicated at block 926, and it is determined whether the input protocol statement value(s) is valid, as indicated at block 928.

If it is determined that the input protocol statement value(s) is invalid (e.g., outside of a pre-defined numerical range, or the like), notification is presented, as indicated at block 930. Subsequently, it is determined whether the user desires to continue despite the invalid value or correct the value entry. This is indicated at block 932. If the user desires to correct the value entry, a corrected value associated with the protocol statement is received, as indicated at block 934, and the user is returned to the step indicated at block 928 wherein it is determined if the corrected value associated with the selected protocol statement is valid.

If it is determined at block 928 that the value associated with the selected protocol statement is valid or if it is determined at block 932 that the user desires to continue despite an invalid value entry (and that the user has authority to override the invalid entry indication), it is subsequently determined whether input of a value associated with another protocol statement is desired. This is indicated at block 936. If it is determined that input of a value associated with another protocol statement is desired, the user is returned to the step indicated at block 922 and user selection of a protocol statement is received. If, however, it is determined at block 936 that the user does not desire to input a value associated with another protocol statement, the input value is stored in association with the protocol statement, as indicated at block 938.

Subsequently, as indicated at block 940, it is determined whether a value associated with any other protocol statement is required for completion of the protocol order. If it is determined that another value is required for completion of the protocol order, the status is subsequently updated to, for instance, "In-Process", as indicated at block 942. If, however, it is determined at block 940 that no additional protocol statement values are required, the status is updated to, for instance, "Complete", as indicated at block 944.

As can be understood, embodiments of the present invention provide computerized methods and systems for creating and documenting protocol orders in, for instance, a molecular diagnostic laboratory environment. Utilizing the methods and systems described herein, protocol statements may require values to be entered in association therewith prior to permitting access to subsequent protocol orders. Accordingly, more accurate test runs and, consequently, more accurate test results, may be achieved. Additionally, as values associated with protocol statements are electronically captured, in accordance with embodiments hereof, such values may be searched to evaluate trends or identify protocol orders and/or results that may be affected by a later discovered error or the like.

Embodiments of the present invention further provide computerized methods and systems for associating a plurality of protocol orders or containers with one another into a batch. Embodiments further provide for sharing of values entered in association with shared protocol statements among the members of a batch. Sharing of protocol statement values saves time for the laboratory technologist as common values, e.g., lot numbers, run temperatures, and the like, need only be input one time instead of independently entered for all members of a batch.

Additional embodiments of the present invention provide computerized methods and systems for proactively notifying a user if a changed protocol statement or protocol statement value will affect other protocol orders and/or results. Thus, if it is discovered, for instance, that an incorrect DNA purity value range had been input when a worksheet for a particular protocol order was built or an incorrect run temperature had been input as a value associated with a particular protocol statement, upon changing the protocol statement or protocol statement value, respectively, the user will be notified of all other protocol orders and/or results that also utilized the incorrect protocol order and/or protocol statement value. The user can then quickly determine what other changes may be necessary to facilitate more accurate results reporting.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more non-transitory computer storage media having computer-executable instructions embodied thereon that, when executed by a processor, cause the process to perform for performing a method for defining a plurality of protocol orders, the method comprising:

receiving a plurality of protocol orders, each protocol order of the plurality of protocol orders associated with a different patient;

creating a batch by receiving user input associating two or more protocol orders of the plurality of protocol orders, the two or more protocol orders comprising a same series of steps, completion of the same series of steps producing a result for each of the two or more protocol orders;

identifying a common data element shared by the two or more protocol orders;

receiving input of a value for the common data element in association with a first protocol order of the two or more protocol orders associated with one another in the batch; and upon receiving the received value for the first protocol order of the two or more protocol orders, automatically associating the received value with each of the remaining protocol orders of the two or more protocol orders associated with one another in the batch.

2. The one or more computer storage media of claim 1, wherein receiving user input associating the two or more protocol orders comprises receiving manually entered user input.

3. The one or more computer storage media of claim 1, wherein receiving user input associating the two or more protocol orders comprises receiving user selection of protocol orders from a worklist.

4. The one or more computer storage media of claim 1, wherein receiving user input associating the two or more protocol orders comprises receiving user-defined protocol-order criteria.

5. The one or more computer storage media of claim 4, wherein the method further comprises searching at least one data store for protocol orders that satisfy the user-defined protocol-order criteria.

6. The one or more computer storage media of claim 1, wherein the method further comprises associating the batch with a batch identifier.

7. The one or more computer storage media of claim 1, wherein the method further comprises searching a database for a matching batch upon receiving input of the batch identifier.

8. The one or more computer storage media of claim 1, wherein the method further comprises associating the plurality of protocol orders in a sequential order such that a subsequent protocol order is accessible upon receiving input of a value associated with a previous protocol order.

* * * * *